Figure 1:
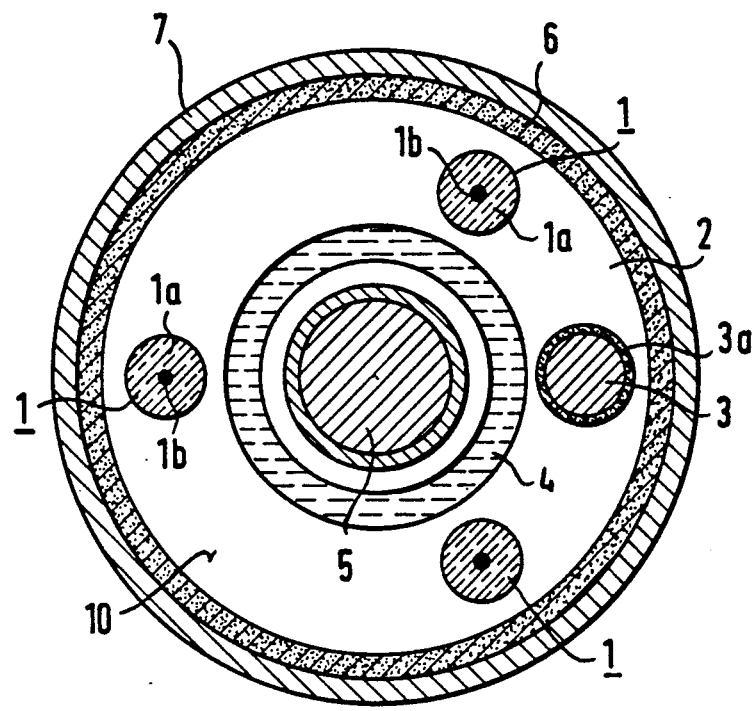

United States Patent [19]

Ahsbahs et al.

[11] Patent Number: 5,007,424
[45] Date of Patent: Apr. 16, 1991

[54] POLAROGRAPHIC/AMPEROMETRIC MEASURING SENSOR

[75] Inventors: Walter Ahsbahs, Merzhausen; Helmut Leist, Waldkirch, both of Fed. Rep. of Germany

[73] Assignee: Hellige GmbH, Freiburg, Fed. Rep. of Germany

[21] Appl. No.: 547,528

[22] Filed: Jun. 29, 1990

Related U.S. Application Data

[63] Continuation of Ser. No. 236,108, Aug. 1, 1988.

[30] Foreign Application Priority Data

Aug. 3, 1987 [EP] European Pat. Off. ........ 87111196.9

[51] Int. Cl.[5] .......................................... G01N 27/404
[52] U.S. Cl. .................................... 128/635; 204/403; 204/412; 204/415
[58] Field of Search ....................... 204/403, 412, 415; 128/635

[56] References Cited

U.S. PATENT DOCUMENTS

| | | | |
|---|---|---|---|
| 3,260,656 | 7/1966 | Ross, Jr. .................................. | 204/1 |
| 4,302,315 | 11/1981 | Stetter et al. ........................ | 204/412 |
| 4,419,210 | 12/1983 | Wang ................................... | 204/403 |
| 4,729,824 | 3/1988 | Giner .................................... | 204/415 |
| 4,871,440 | 10/1989 | Nagata et al. ........................ | 204/403 |

Primary Examiner—G. L. Kaplan
Attorney, Agent, or Firm—John E. Curley; Kenneth J. Stachel

[57] ABSTRACT

This invention provides a polarographic/amperometric measuring sensor, particularly useful for transcutaneous determination of the oxygen partial pressure (tcpO$_2$) in the blood by means of a Clark-type electrode arrangement. According to the invention the counter electrode, preferably made of a noble metal, is disposed about the insulating material encasing the working electrode and is preferably made of the same noble metal as the working electrode. The measuring sensor can also be provided with a pH electrode for simultaneous determination of the carbon dioxide partial pressure (tcpCO$_2$) in the blood.

18 Claims, 3 Drawing Sheets

POLAROGRAPHIC/AMPEROMETRIC MEASURING SENSOR

This application is a continuation of application Ser. No. 07/238,108, filed Aug. 1, 1988, and now abandoned.

FIELD OF THE INVENTION

The invention relates to a measuring sensor for the transcutaneous determination of the oxygen partial pressure ($tcpO_2$) in the blood of a living organism by means of a polarographic/amperometric measuring sensor having a Clark-type electrode arrangement, in which, exposed on the measuring face and covered by an electrolyte layer over which a thin membrane is stretched, at least one cathode embedded in an insulating material and at least one noble metal anode are disposed in the working face of the sensor at least a portion of the working face functioning as a reference electrode.

BACKGROUND OF THE INVENTION

Transcutaneous oxygen partial pressure ($tcpO_2$) measurements have hitherto usually been carried out by polarography/amperometry, for example using a two-electrode arrangement. However, a particular problem which arises with this is that a silver/silver chloride layer is formed by anodic chlorination, because the anode and the reference are combined as one electrode composed of silver when a chloride ion-containing electrolyte is used. An electrode arrangement of this known type is also unsatisfactory with regard to its long-term operating stability. Electrolytic silver transport to the cathode takes place, with deposition of silver on the cathode, especially with so-called microcathodes, resulting in a change in its area and thus in the $pO_2$ measuring current. Occasionally, there is formation of rapidly growing silver dendrites, especially when electrolyte layer thickness is only a few microns.

On simultaneous transcutaneous measurement of the carbon dioxide partial pressure ($tcpCO_2$) by the Stow-Gertz-Severinghaus method in the same electrolyte using a combined measuring sensor there is, moreover, an effect on the pH by the cathodic production of hydroxyl ions.

Figure 2:
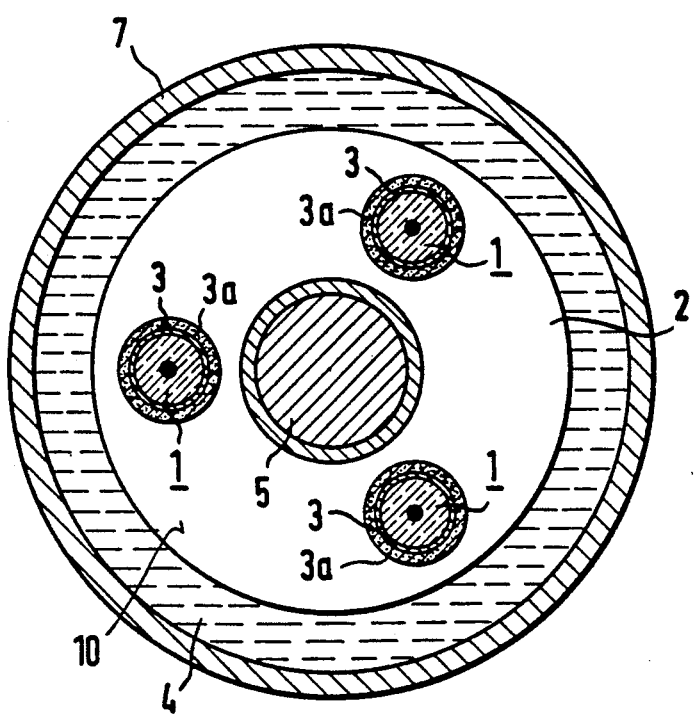

A known three-electrode arrangement for polarographic/ amperometric $pO_2$ measurement is available for eliminating these effects, as has been described, for example, by Severinghaus for a combined measuring sensor in "Journal of Applied Physiology", Vol. 51/1981, pages 1027–1032 (cf. in particular FIG. 2 on page 1028). In a multiple electrode arrangement of this type the function of anode and reference electrode are divided, so that there is, in particular, some freedom in the choice of material for the anode so that, for example, platinum, or gold can be used or, inter alia, the same material as that for the cathode. It is possible in this way to bring about consumption of the same number of hydroxyl ions at the anode as have been generated at the cathode.

However, with the thin electrolyte layer which is necessary for transcutaneous measuring sensors it is found that, in contrast to the customary dimensions, the reference electrode must, for reasons of stability, especially in the said combined sensor, be designed with a relatively large surface area, whereas the counter electrode (anode) ought rather to have a smaller area. However, once again a certain silver ion concentration develops in the electrolyte, which again results in silver deposits on the cathode. The measuring faces of sensors of this type must therefore be polished from time to time, and especially before each new series of measurements. This also applies to the abovementioned combined measuring sensor described by Severinghaus.

OBJECT OF THE INVENTION

Thus the object of the invention is to provide improved $tcpO_2$ measuring sensors and/or the said combined $tcpO_2/tcpCO_2$ measuring sensors that avoid interfering silver deposits on the cathode which, in particular, alter the $pO_2$ measuring current, and produce undesired changes in the hydroxyl ion concentration in the electrolyte.

SUMMARY OF THE INVENTION

For a transcutaneous measuring sensor of the type mentioned in the introduction, the invention is characterized in that the anode or counter electrode (preferably formed of a noble metal) is disposed at least partially around the insulating material (usually glass) encasing the cathode.

According to the invention, the anode is formed as a curved surface or ring which encloses the cathode at least in the region of the measuring face, and which separates the reference electrode surface geometrically from the cathode. The anode, i.e. the counter electrode, is thus not arranged remote from the cathode as in the prior art. Nor is there a point arrangement of an anode inside the reference electrode surface area, as is also the case in other known $pO_2$ or $pO_2/pCO_2$ measuring sensors.

The advantageous effect of this novel design of the anode makes it possible to choose for the anode, a material which has a sufficiently more positive potential than that of the reference electrode in the case of potentiostatic control. This results in a potential threshold for silver ions which they are unable to overcome when the electrolyte layer is thin, thus preventing silver deposits on the cathode. Thus, it is no longer necessary to polish the measuring face of the measuring sensor to remove silver deposits. This is a great advantage for measurement using transcutaneous measuring sensors of this type in routine clinical practice.

If the anode is designed preferably as a narrow ring encircling the cathode there is no adverse effect on the reference electrode and the electrolyte potential is unambiguously determined by the reference electrode potential.

The anode can, for example, be wound as a thin sheet of noble metal around the insulating material of the cathode, or deposited by evaporation or sputtering especially in the case of so-called microcathodes, wherein the cathode is typically sealed in a glass tube.

The distance between the anode and cathode therein is usually so small that even an uncontrolled fall in voltage at the cathode is unimportant when the $pO_2$ measuring current is small.

Another advantage of the invention is the effect of the generation of oxygen at the anode being at the smallest possible distance from the consumption of oxygen at the cathode. In this way the disadvantage of the oxygen consuming measurement, caused by an oxygen gradient, even within the skin, and thus a measurement deviation which cannot be calibrated beforehand, can be reduced or entirely eliminated.

Another advantageous effect of the invention is surprisingly, that silver deposition at the cathode, and as a consequence thereof a drift in the $pO_2$ measuring current or in another polarographic/amperometric measuring current (for example with simultaneous $tcpCO_2$ measurement), does not occur even when the noble metal ring or coating forming the anode are not connected through an external circuit so that the current finally flows to the reference electrode.

However, in this case the measuring current will flow from the reference electrode via the noble metal of the anode, it being possible to regard the anode with the reference electrode as, for example, a Pt-Ag/AgCl cell or Au-Ag/AgCl cell with an e.m.f. (values from $-40$ mV to $-60$ mV and from $+10$ mV to $+30$ mV) and an internal resistance. This cell does not adversely affect the amperometric measurement, and the noble metal anode does not in turn initially pass any silver ions to the cathode. In the best case, such are deposited on the anode itself.

In order to ensure that, even on prolonged operation, no coating of the noble metal anode with silver takes place, and thus silver ions are again able to reach the cathode, an external (or even integrated internal) electrical connection between the noble metal of the anode and the Ag/AgCl reference electrode may be provided. Measurements have shown that this electrical connection has no adverse effects as long as the noble metal anode is designed to have a small area compared with the area of the reference electrode, which will usually always be the case, especially when, as is customary, microcathodes are used. The result of this is that the cathode current, by reason of the concentration of the electric field onto the nearest metal edge, flows to the noble metal anode, as long as the said thin electrolyte layer is present in the region of it, and not to or along the Ag/AgCl reference electrode, so that active silver transport is avoided.

The desired thin electrolyte layer in the region of the noble metal anode can also be ensured when an electrolyte reservoir is provided in the measuring face of the measuring sensor and is designed, for example, as a semi-annular groove. In an advantageous embodiment of the invention, this electrolyte reservoir extends radially between the cathodes encircled by the anode when for example, three or more microcathodes are used.

THE DRAWINGS

Figure 3:
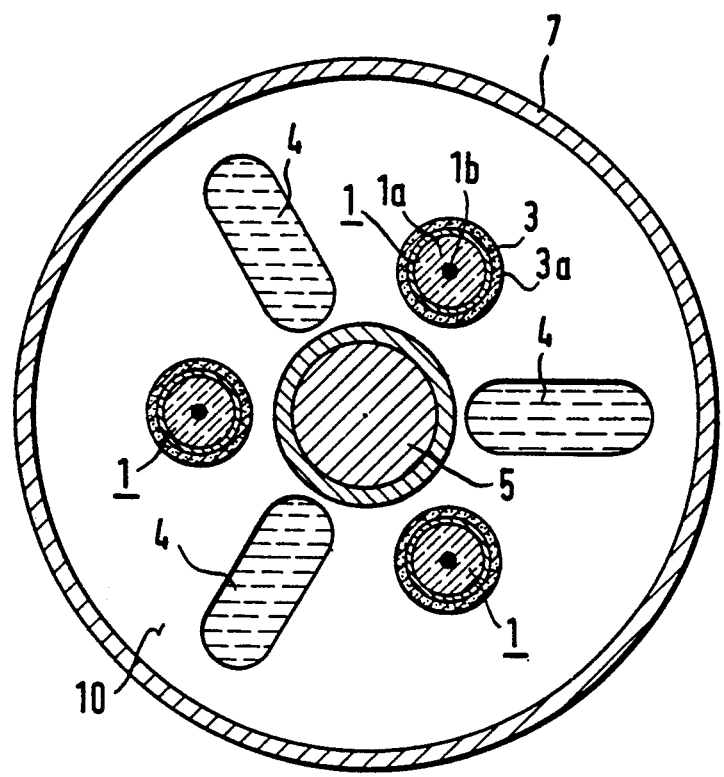
Figure 4:
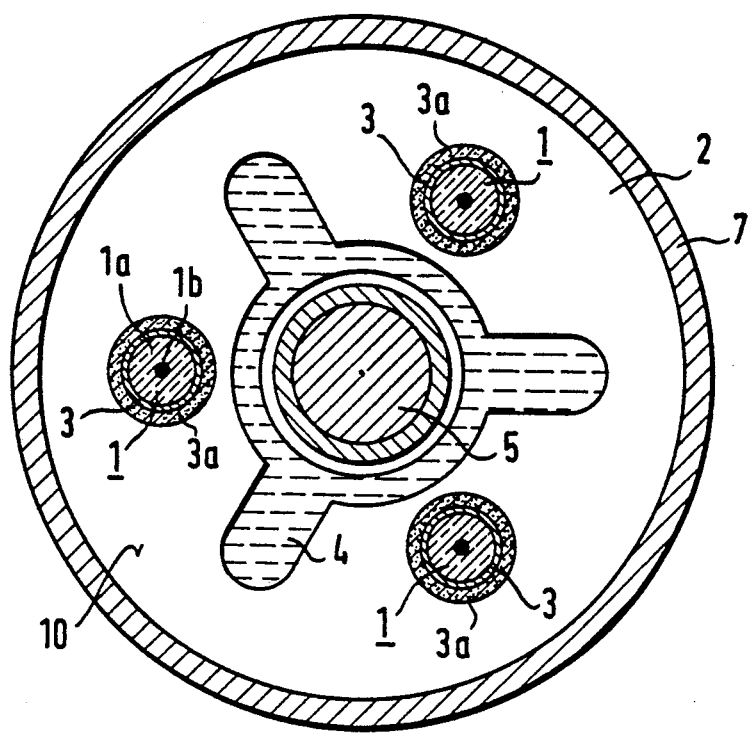
Figure 5:
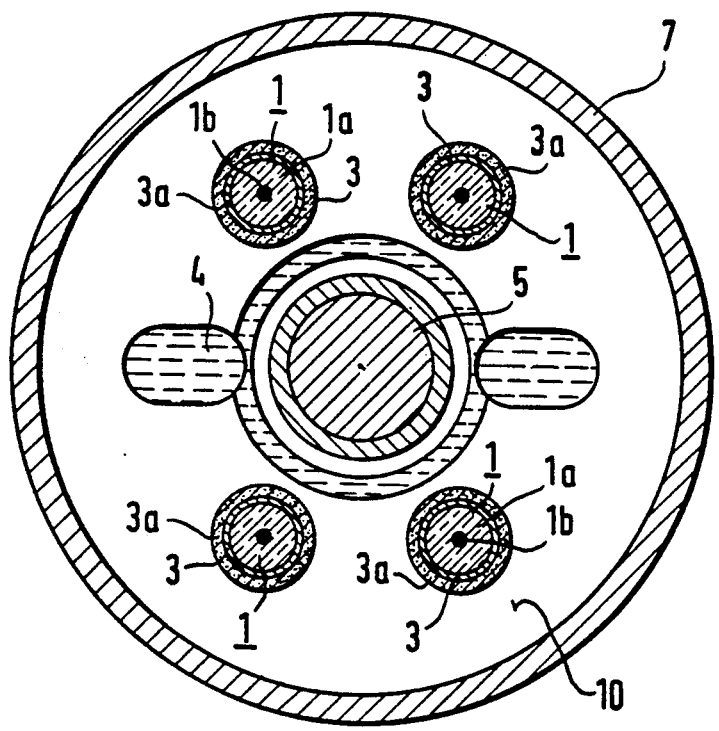

The invention and advantageous details are further illustrated hereinafter by the drawings based on exemplary embodiments. In the drawings:

FIG. 1 shows, for comparative illustration, a plan of the measuring face of a transcutaneous $pO_2/pCO_2$ measuring sensor corresponding to the state of the art, FIG. 2 shows a first exemplary embodiment of a measuring sensor having features according to the invention, likewise depicted as a combined $pO_2/pCO_2$ sensor, FIG. 3 shows a modified embodiment of a measuring sensor having features according to the invention and having an advantageous arrangement of several electrolyte reservoirs in the measuring face, FIG. 4 shows an advantageous modification of the arrangement depicted in FIG. 3; and FIG. 5 shows another design of the measuring face of a measuring sensor having features according to the invention three cathodes being replaced by provision of two pairs of cathodes plus an electrolyte channel according to the concept of FIG. 4.

The diagrammatic plan view, the scale of which is enlarged approximately 10:1, of the measuring face of a known combined $pO_2/pCO_2$ measuring sensor corresponding, in principle, to the design of Severinghaus in the abovementioned citation, illustrates, as the spatially largest part of the electrode arrangement, an Ag/AgCl reference electrode 2 which can also be replaced, in a known manner, by another suitable solid reference. An encircling insulating layer 6 is enclosed by the edge 7, on which the measuring membrane is gripped in a manner known from Clark, of the measuring face. The measuring sensor shown in FIG. 1 contains, for example, three microcathodes 1 which pass through the reference body at right angles to the plane of the drawing and which are formed, for example, by a platinum wire 1b which is sealed in a glass tube 1a, is exposed on the polished measuring face depicted, and is connected on the opposite end remote from the measuring face, in a known manner, to a measuring circuit, whose first part (for example preamplifier stage) may also itself be integrated in the housing of the measuring sensor. The counter electrode or anode, for example made of platinum or gold, indicated by reference 3, may be encircled by a thin insulating sheathing 3a. The anode 3 is exposed in the plane of the measuring face, likewise polished flat as the surfaces of the cathodes 1; the anode 3 is likewise connected, on the side remote from the measuring face in the housing of the measuring sensor, to a connecting cable or to a preprocessing integrated circuit. In the axis, that is to say in the central position of the measuring sensor, there is shown a pH electrode 5, which can be designed as a glass electrode or, with particular advantages, as an iridium/iridium oxide electrode according to EP-A 0,102,033. In the depicted embodiment, the pH electrode 5 provided for $CO_2$ concentration determination is encircled by an annular groove which acts as electrolyte reservoir. The purpose and particular advantage of an electrolyte reservoir of this type located in the measuring face are known to those skilled in the art and, for example also explained in the abovementioned Severinghaus citation. However, in the design of a combined measuring sensor described by Severinghaus, the electrolyte reservoir is formed by a circular groove segment with the anode being located in one of these groove segments.

In contrast to the known embodiment shown in FIG. 1, in the first exemplary embodiment of the invention shown in FIG. 2, each anode 3 is formed by a thin noble metal coating which encircles the glass insulating material 1a of each microcathode 1 and is in turn electrically separated from the reference electrode 2 by an insulating layer 3a. Thus each cathode 1 is geometrically separated from the reference electrode 2 by an associated annular anode 3. The anodes can, as mentioned, be formed by a thin sheet of noble metal or, advantageously, by deposition by evaporation or sputtering, as well as by other coating techniques. Each anode 3 is, where appropriate, electrically conducted out to the end of the measuring sensor which is remote from the measuring face, for example by the anode 3 being continued as a sheath-like encasing of the cathodes in the axial direction at right angles to the plane of the drawing. The groove-like recess 4, as electrolyte reservoir, is located in a position which is radially further outwards. This makes it possible for the electrolyte reservoir to be larger than that in FIG. 1, and for the heating area in the neighborhood of the cathodes to be larger than in the embodiment shown in FIG. 2.

In the embodiment shown in FIG. 3, the design of the measuring face of the combined $pO_2/pCO_2$ measuring sensor is somewhat different from that of the embodiment shown in FIG. 2. In this case, there are three radial grooves or channels 4 as electrolyte reservoir, each being in a position which divides the angular distance between the cathode/anode assembly 1, 3. This ensures, when the electrolyte volume is adequate, that there is a satisfactory supply of electrolyte to all the electrodes.

It has also been determined that deposition of silver on the cathode is also considerably reduced when the measuring face itself does not contain an Ag/AgCl reference, and the silver in the face remains shiny or is even insulated, and only one or a few reference points in the form of Ag/AgCl are formed, or the silver is chlorinated only at these points. Suitable and preferable for this purpose are the mechanically protected electrolyte channels 4.

The arrangement shown in FIG. 4 combines the arrangement of the electrolyte channel 4 shown in FIG. 1 and FIG. 3 in such a way that the supply of electrolyte to the central pH electrode 5 is even further improved compared with FIG. 3, while simultaneously maintaining the available electrolyte volume and the heating area in the neighborhood of the cathode.

The arrangement shown in FIG. 5 shows a variant of the arrangement of FIG. 4, having four instead of three cathode/anode assemblies.

A particularly advantageous embodiment results when the Ag/AgCl reference is formed wholly or mainly only in the electrolyte channels 4, which results in less AgCl dissolving and being available in the neighborhood of the cathode.

With the radial electrolyte channels in the embodiments in FIGS. 3, 4 and 5, uniform distribution of the electrolyte reservoir in the neighborhood of all electrodes is achieved.

The electrode arrangement provided according to the invention is also of importance for measurements with catheters, there being no heat-conducting material provided for thermostatic purposes. The method can also be applied generally to Clark polarographic/amperometric measuring arrangements, that is to say also for the cathodic reduction of other substances, for example $N_2O$, or for the anodic oxidation of, for example, alcohols, it likewise being possible to avoid, or at least reduce, deposits which interfere with the measurement, by the introduction, according to the invention, in this case of a counter electrode (the anode for $pO_2$) disposed between the working electrode (the cathode for $pO_2$) and reference electrode (Ag/AgCl in the above case). This ring can, in place of noble metal such as platinum or gold, also be formed of other inert conducting materials such as graphite or conducting glasses or plastics or doped semiconductors such as silicon, gallium arsenide, germanium and the like. For example, it is possible in this way for the structure to be monolithic or produced by coating techniques.

Although, the invention has been described in considerable detail by the foregoing, it is understood that many variations can be made therein without departing fromt he spirit and scope thereof as defined by the appended claims.

We claim:

1. A sensor element particularly adapted for transcutaneous, polarographic/amperometric measurement of oxygen partial pressure in the blood of a living organism, said sensor element having a body portion made of heat conducting insulating material and a measuring face at least a portion of the area of which constitutes a reference electrode surface, said measuring face having a gas permeable membrane tautly stretched thereover, a layer of electrolyte material dispersed between the said measuring face and the said gas permeable membrane, said measuring face also having disposed in the plane thereof at least one electrode assembly comprising a working electrode, a layer of insulating material completely surrounding the working electrode, said working electrode having a counter electrode completely surrounding said working electrode and disposed peripherally of the layer of insulating material to thereby separate said working electrode and said counter electrode with the said layer of insulating material and a sheath of insulation encircling said counter electrode to separate electrically said counter electrode from said reference electrode.

2. The sensor element of claim 1 wherein the working electrode is the cathode and the counter electrode is the anode.

3. The sensor element of claim 2 wherein the cathode is formed integrally with the layer of insulating material by encasing a thin noble metal wire concentrically in a glass tube.

4. The sensor element of claim 3 wherein the anode comprises a thin sheet of noble metal disposed about the glass tube encasing the cathode.

5. The sensor element of claim 3 wherein the anode comprises a coating of noble metal on the surface of the glass tube encasing the cathode.

6. The sensor element of claim 1 wherein a plurality of electrode assemblies are disposed in the plane of the measuring face each electrode assembly being spaced substantially equidistantly from the center of the measuring face.

7. The sensor element of claim 6 wherein the electrode assemblies are spaced at substantially the same angular distance from each other.

8. The sensor element of claim 1 wherein the anode and cathode are each formed of noble metal.

9. The sensor element of claim 8 wherein the anode and cathode are each formed of the same noble metal.

10. The sensor element of claim 1 having a direct electrical connection between the reference electrode surface and the counter electrode.

11. The sensor element of claim 1 wherein the reference electrode surface is comprised of silver/silver chloride.

12. The sensor element of claim 1 wherein the measuring face is provided with an electrolyte storage resevoir.

13. The sensor element of claim 12 wherein the electrolyte storage resevoir comprises a plurality of recesses arranged at substantially the same angular distance from each other.

14. The sensor of claim 13 wherein the radially extending recesses are interconnected by a channel.

15. The sensor element of claim 12 wherein the reference electrode surface is comprised of silver which is chlorinated only in the region of the electrolyte storage resevoir.

16. The sensor element of claim 1 wherein a pH measuring electrode is disposed in the plane of the measuring face to enable transcutaneous measurement of carbon dioxide partial pressure in the blood.

17. The sensor element of claim 16 wherein the pH measuring electrode is comprised of iridium/iridium oxide.

18. The sensor element of claim 1 wherein the reference electrode and the counter electrode are electrically connected.

* * * * *